United States Patent [19]

Dillard, III

[11] Patent Number: 4,708,791
[45] Date of Patent: Nov. 24, 1987

[54] WATER QUALITY MONITOR
[75] Inventor: John A. B. Dillard, III, Ojai, Calif.
[73] Assignee: PJD Associates Inc., Santa Barbara, Calif.
[21] Appl. No.: 938,060
[22] Filed: Dec. 4, 1986
[51] Int. Cl.$^4$ .............................................. B01D 13/00
[52] U.S. Cl. .................................................. 210/96.2
[58] Field of Search ...................... 210/34.1, 96.2, 652, 210/85; 340/603; 364/552

[56] References Cited
U.S. PATENT DOCUMENTS
4,660,152 4/1987 Downing et al. ............... 364/552 X Primary Examiner—Frank Spear
Attorney, Agent, or Firm—Harry W. Brelsford

[57] ABSTRACT

A pair of probes is disposed in a pipe supplying water that has been treated to reduce inorganic solids to a selected level. A supply voltage is impressed across the probes to create a signal voltage that is a measurement of the ionization potential in the water between the probes. A dip switch and resistors of progressively different values are connected across the voltage source, and one switch of the dip switch is manually closed that represents the upper limit or range of desired dissolved solids. A signal voltage is created by the dip switch resistor, and the probe voltage and the dip switch voltage are supplied to an amplifier. If the difference on the two voltages is high, then a flip-flop energizes a red light indicating excessive solids; and if the difference is small, then the flip-flop energizes a green light showing an acceptable level of solids.

4 Claims, 2 Drawing Figures

WATER QUALITY MONITOR

FIELD OF THE INVENTION

This invention relates to the monitoring of water quality, for drinking or commercial use, to indicate when the total dissolved inorganic solids exceed or are less than a preselected limit. The monitoring is useful to monitor water wherein solids are reduced, such as by reverse osmosis and is also useful to monitor water where the solids are removed by dionizing apparatus.

BRIEF DESCRIPTION OF THE INVENTION

Two probes are inserted in the water to be tested and a voltage is impressed between the probes. The current flow between the probes is a measure of the ionization potential in the water and therefore an indication of the amount of total dissolved inorganic solids (TDS). A dip switch connected to a large number of resistors permits the operator to select one of the switches calibrated to a specific level of TDS, such as 100 or 200 parts per million. An indicator is provided to show whether the water quality is above or below the selected setting. Lights are presently preferred as indicators, a red light showing dissolved solids in excess of the selected setting and a green light showing dissolved solids less than the selected setting. If the monitor is used in connection with a reverse osmosis or other ion removing device, the red light indicates a need to service the water purification equipment.

DESCRIPTION OF THE DRAWINGS

Referring to the drawings forming an integral part of this specification.

DETAILED DESCRIPTION

Figure 1:
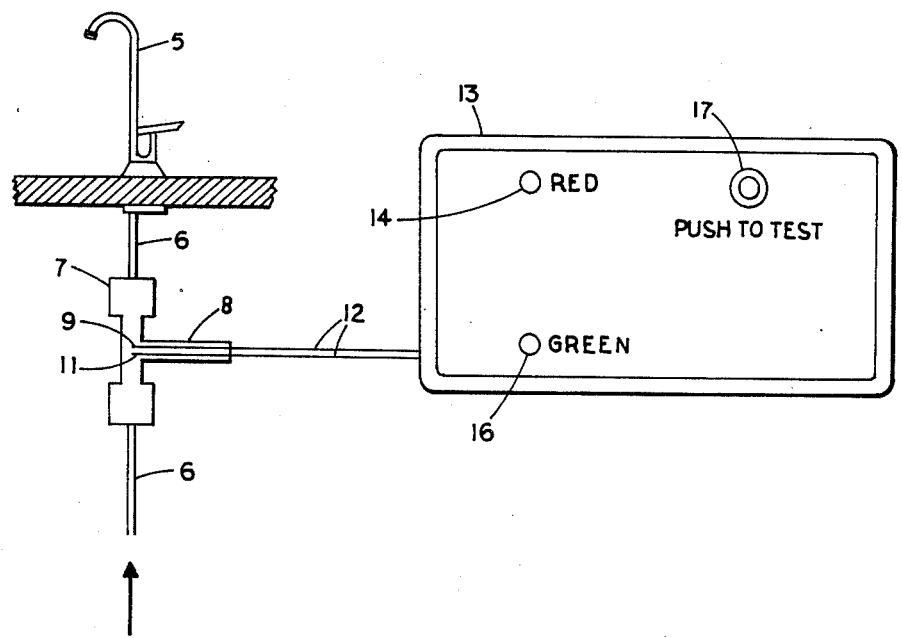
FIG. 1 is a diagram of the device with probes inserted in a pipe leading to a drinking water faucet, and with a housing containing a manual switch to initiate a measurement, a red light to indicate excessive solids and a green light to indicate an acceptable level of solids.

Referring to FIG. 1, a water faucet 5 is connected to a supply pipe 6 of any suitable material. Inserted in the pipe 6 is a plastic tubular member 7 having a solid projection 8 that carries two probes 9 and 11. The material of the tube 7 and the solid projection 8 are made of electrical non-conducting material such as a suitable plastic.

The probes 9 and 11 are connected by wires 12 to a housing 13 that has a red light 14 that when energized indicates dissolved solids in excess of a selected quantity, and a green light 16 that when energized indicates dissolved solids less than a selected quantity. The device is preferably not normally energized and an operator presses a switch button 17 to energize the circuit and impress a voltage across tha probes 9 and 11 and cause either the red light 14 or the green light 16 to be illuminated. The device is preferably operated when there is no flow to the faucet 5 inasmuch as flowing water sometines gives eratic results.

FIG. 2

Figure 2:
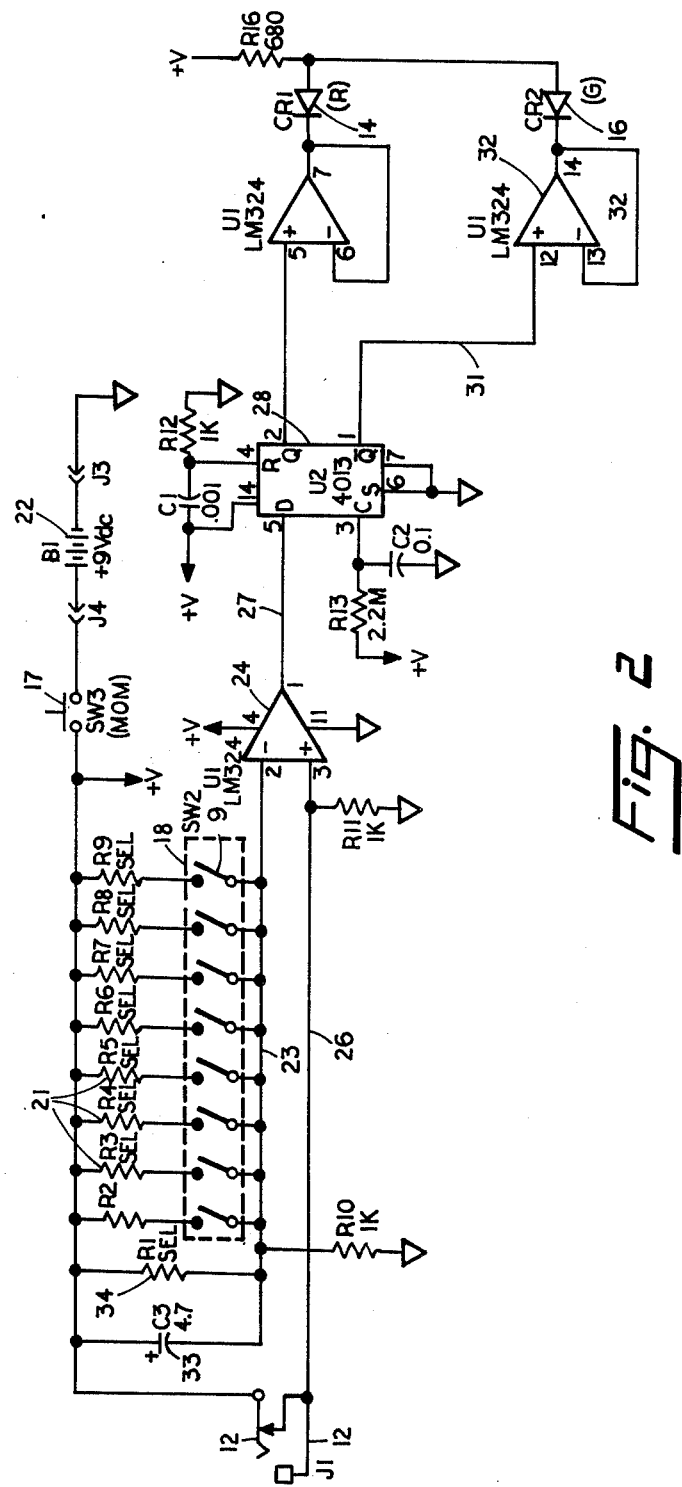
FIG. 2 is a schematic circuit showing a dip switch for selecting the setting level, a red light and associated amplifier and a green light and associated amplifier.

Referring to FIG. 2, a dip switch assembly 18 has a plurality of switches 19 each connected in series to a resistor 21. The resistance of each resistor 21 is different, increasing in resistance from left to right. The dip switches 19 and associated resistors are connected to a source of voltage 22 and a 9 volt battery is presently preferred. The operator closes only one of the dip switches 19 and the calibration in parts per million of solids of each switch and resistor combination is preferably written at each switch. On FIG. 2 resistors 21 are R2 to R9.

All of the dip switches 19 are connected to a bus 23 which is connected to an amplifier 24. The output from the probes 9 and 11 is carried by a wire 26 to the same amplifier 24. The output of the amplifier 24 is connected by a wire 27 to a flip-flop 28. One state of the flip-flop transmits a signal to an amplifier 29 which causes the red light 14 to be illuminated. The other state of flip-flop 28 is connected by a wire 31 to an amplifier 32 which causes that green light 16 to be illuminated.

A capacitor 33 and a resistor 34 are connected from the voltage source to the bus 23. On FIG. 2, 34 is also R1.

OPERATION

The operator first selects one of the dip switches 19 corresponding to a selected quantity of dissolved solids in the water, for example the setting of 100 or 200 parts per million. The operator next manually closes switch 17 causing current to flow through the selected resistor 21 to create a voltage on bus 23. Closing switch 17 also places a voltage across the probes 9 and 11 (FIG. 1) and the ionized solids in the stationary water in tube 7 cause a current to flow, creating a voltage at wire 26.

The difference in voltage present on wire 23 and 26 is amplified by amplifier 24 and the output is fed by wire 27 to the flip-flop 28. If the probe voltage is less than the voltage on bus 23 then the flip-flop energizes the green light 14 and if more then the flip-flop energizes the red light 16. The red light advises the operator that the reverse osmosis or deionizing equipment, as the case may be, needs servicing or attention.

CIRCUIT COMPONENTS

The probes 9 and 11 are preferably of 316 stainless steel imbedded in FDA approved polyethelene. An 8 switch dip switch is satisfactory and a nine volt battery or nine volt transformer is preferred to avoid any dangerous voltages. The values of resistors 21 are not increased linearly but must be nonlinear in progressive value. The resistors are preferably ¼ to ⅛ watt and 2%. The selected values for deionized water are much different from water treated by reverse osmosis inasmuch as very low quantities of solids are needed for boilers and other equipment requiring substantially no ions. The following table of values has proved useful for deionized "DI" and reverse osmosis "RO."

| R1 | DI variable 100 to 18 meg | RO variable 100 to 18 meg | RO ppm |
|---|---|---|---|
| R2 | 10K | 14.0K | 50 |
| R3 | 20K | 10.4K | 75 |
| R4 | 50K | 8.52K | 100 |
| R5 | 100K | 6.30K | 150 |
| R6 | 200K | 4.55K | 200 |
| R7 | 500K | 3.85K | 250 |
| R8 | 1 MEG | 3.48K | 300 |
| R9 | 2 MEG | 2.27K | 500 |

The resistances could be varied for the RO column to overlap the DI range, in which case the RO range could vary from 20K to 100 ohms. The resistances for DI measurement can vary from 20K to 18 megohms. The amplifiers are preferably quads, only 3 are used, and U1-LM324 is preferred. The flip-flop is preferably U2-4013. The lights are preferably LED, TI, ¾ red and green.

The entire circuit is independent of any voltage fluctuations from the source 22.

The invention has been described with reference to a presently preferred embodiment as required by the statutes. It will be apparent to those skilled in the art that modifications and variations can be made. For example the device can be operated by alternating current with minor circuit revisions. Also, all of the dip switches can be left open and the valve of R1 can be selected from the table of resistances, to get a single reading instrument. There are included within the scope of the following claims all modifications and variations that come within the true spirit and scope of the invention.

I claim:

1. The combination of an ionization potential probe and a qualitative indicating circuit wherein the circuit includes:
   (a) a source of voltage connected to the probe;
   (b) a dip switch having resistors of progressive quantity of resistance connected to each switch of the dip switch and each switch and resistor being connected to the source of voltage;
   (c) an amplifier connected to the dip switch and to the probe and having an output depending upon the difference in voltage between probe and the dip switch;
   (d) a flip-flop connected to the amplifier output and having two outputs;
   (e) a first indicator connected to one output of the flip-flop;
   (f) a second indicator connected to the other output of the flip-flop, whereby a large current flow at the probe produces a voltage different from a selected dip switch voltage to activate an indicator to indicate excessive dissolved inorganic solids and a small difference voltage activates the other indicator for an acceptable level of dissolved solids.

2. The combination of claim 1 wherein the dip switch resistances vary from about 20K to 100 ohms to test for dissolved solids in water treated by reverse osmosis.

3. The combination of claim 1 wherein the dip switch resistances vary from about 20K to 18 megohms to test for water treated by deionizing apparatus.

4. The combination of claim 1 wherein the flip-flop outputs are amplified and the indicators are LED.

* * * * *